United States Patent [19]

Goel et al.

[11] Patent Number: 5,484,930
[45] Date of Patent: Jan. 16, 1996

[54] CHIRAL ETHYL [6–AMINO–4–[ [12–(METHOXYMETHYLAMINO)–1– METHYL–2–OXOETHYL]AMINO] –5–NITRO–2–PYRIDYL]CARBAMATE

[75] Inventors: Om P. Goel; Sham S. Nikam, both of Ann Arbor, Mich.

[73] Assignee: Warner-Lambert Company, Morris Plains, N.J.

[21] Appl. No.: 444,972

[22] Filed: May 19, 1995

Related U.S. Application Data

[62] Division of Ser. No. 836,624, Feb. 13, 1992.

[51] Int. Cl.$^6$ .................................................. C07D 213/75
[52] U.S. Cl. .................................. 546/308; 544/350
[58] Field of Search ................................ 546/308

[56] References Cited

U.S. PATENT DOCUMENTS

| | | | |
|---|---|---|---|
| 4,743,585 | 5/1988 | Hudspeth et al. | 514/17 |
| 4,866,059 | 9/1989 | Temple, Jr. | 514/248 |
| 5,036,053 | 7/1991 | Himmelsbach et al. | 514/19 |
| 5,087,634 | 2/1992 | Reitz et al. | 514/381 |
| 5,095,017 | 3/1992 | Temple, Jr. | 514/249 |

OTHER PUBLICATIONS

Nahm et al., *Tet. Letters*, 22, 3815 (1981).
Schröder, *Chem. Ber.*, 673, 186 (1963).
Cupps et al., *J. Org. Chem.*, 50, 3972 (1985).
Barton et al., *J. Chem. Soc.* (C), 3540 (1971).

*Primary Examiner*—P. I. Dalton
*Attorney, Agent, or Firm*—Todd M. Crissey

[57] ABSTRACT

The present invention relates to compounds of the formula

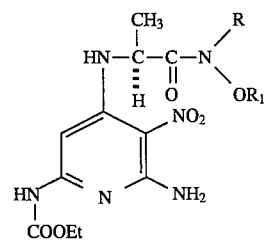

or

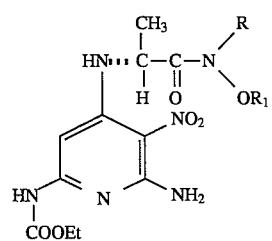

wherein each of R and $R_1$ is a lower alkyl group having from 1 to 4 carbon atoms, which are useful as intermediates to make chiral ethyl (5-amino-1,2-dihydro-2-methyl-3-phenylpyrido[3,4-b]pyrazin- 7-yl)carbamate.

2 Claims, No Drawings

CHIRAL ETHYL [6-AMINO-4-[[12-(METHOXYMETHYLAMINO)-1-METHYL-2-OXOETHYL]AMINO]-5-NITRO-2-PYRIDYL]CARBAMATE

This is a divisional of U.S. application Ser. No. 07/836,624 filed Feb. 13, 1992, now pending.

FIELD OF INVENTION

The present invention relates to a novel chemical process for the preparation of chiral ethyl (5-amino- 1,2-dihydro-2-methyl-3-phenylpyrido[3,4-b]pyrazin-7-yl)carbamate and novel intermediates utilized in said chemical synthesis.

BACKGROUND OF INVENTION

The novel process of the present invention constitutes a markedly improved process for preparing compounds described in U.S. Pat. No. 4,866,059, issued Sep. 12, 1989. The process results in the synthesis of the (S)-(−)- and the (R)-(+)-isomers of ethyl (5-amino-1,2-dihydro-2-methyl-3-phenylpyrido[3,4-b]pyrazin-7-yl)carbamate, which is a known anticancer agent. The present process avoids the need to utilize the chromium trioxide oxidation step described in U.S. Pat. No. 4,866,059, and thus provides a superior process.

SUMMARY OF INVENTION

The novel process of the present invention is set forth in the following reaction scheme.

In the above reaction scheme the * is used to designate that the configuration at the carbon atom is either (S) -(−)- or (R)-(+). The compounds designated by formula (5a) are novel compounds and are a part of this invention. These compounds are further depicted by the following Formulas I and II:

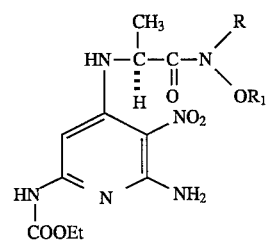

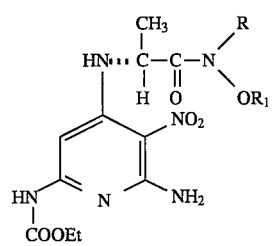

DETAILED DESCRIPTION OF INVENTION

In the above reaction scheme and in formulas I and II, R and $R_1$ mean lower alkyl of from 1 to 4 carbon atoms, i.e.,

REACTION SCHEME I

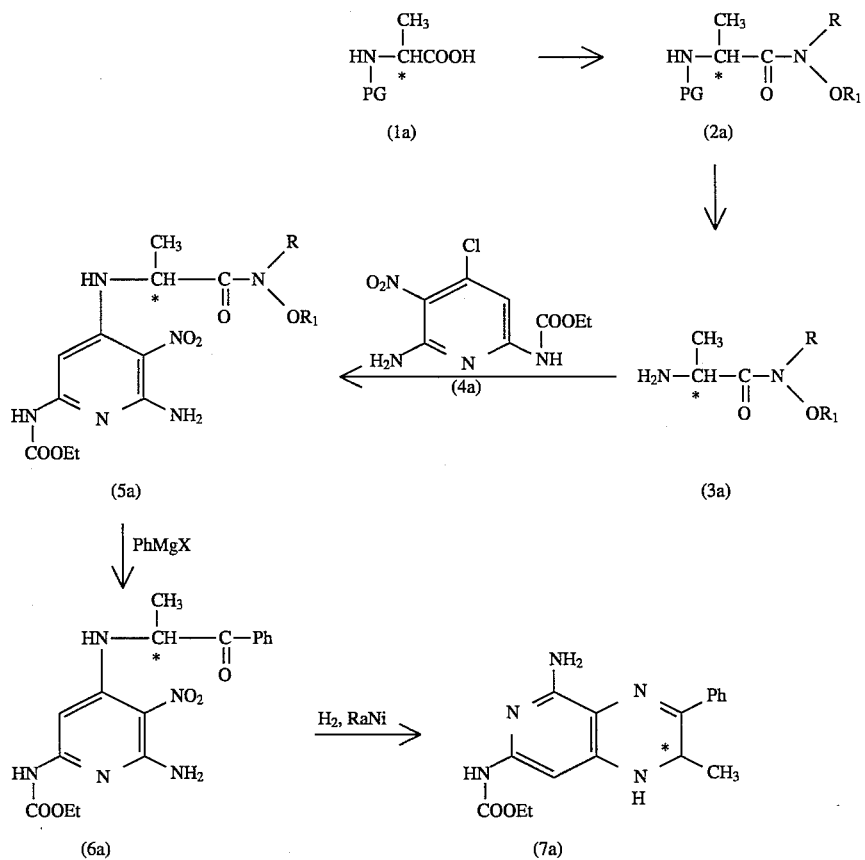

methyl, ethyl, n-propyl or n-butyl. Preferably, each of R and $R_1$ is methyl. In the reaction scheme in the compounds of formulas (1a) and (2a) PG represents a protecting group and can be carbobenzyloxy (phenylmethoxycarbonyl), benzhydryloxycarbonyl, or tert-butoxycarbonyl. The preferred protecting group is carbobenzyloxy. The chiral protected alanine of formula (1a) is treated with a tertiary alkyl amine and a lower alkyl chloroformate in a suitable solvent such as tetrahydrofuran, dioxane, or diethylether, followed by treatment with a di(lower)alkylhydroxylamine in chloroform or dichloromethane. The hydroxylamine has the formula $RNHOR_1$ wherein each of R and $R_1$ is a lower alkyl group having from 1 to 4 carbon atoms. The lower alkyl chloroformate can have an alkyl group which is straight or branched having from 1 to 5 carbon atoms with methyl being preferred. The reaction is carried out at a temperature of from $-25°$ C. to $+25°$ C. with the preferred temperature being $-10°$ C. The lower alkyl tertiary amine can be, e.g., triethylamine or N-methylpiperidine, with the latter being preferred. The resulting amide (2a) is deprotected by catalytic debenzylation when the protecting group (PG) is carbobenzyloxy or benzhydryloxycarbonyl using, e.g., hydrogen gas in the presence of palladium on charcoal in a solvent such as a lower alcohol, e.g., methanol or ethanol or an ether such as dioxane, tetrahydrofuran, or diethyl ether. When the protecting group (PG) in the compounds of formula (2a) is tert-butoxycarbonyl, the protecting group is removed, e.g., by using trifluoroacetic acid which will give compounds (3a) as the trifluoroacetate salt. Without isolation, the compounds of formula (3a) are reacted with ethyl 2-amino-3-nitro-4-chloropyridine-6-carbamate in a lower alcohol solvent such as methanol or ethanol in the presence of a tert-alkylamine such as triethylamine or N-methylpiperidine. When compounds (3a) are in the form of the acetate or trifluoroacetate salt, an extra equivalent of the tert-alkylamine is employed. The carbamates represented by compounds (5a) are treated in a manner as described by Nahm and Weinrab (*Tetrahedron Letters* 22(39):3815–3818 (1981)) with a phenyl Grignard reagent such as phenylmagnesium bromide, phenylmagnesium iodide, or phenyllithium in an ether solvent such as tetrahydrofuran, diethyl ether, or dioxane, and at a temperature of from $0°$ C. to $65°$ C. with the preferred temperature being $0°$ C. The ketones as represented by formula (6a) are reductively cyclized in acetic acid in the presence of Raney nickel to give the desired product (7a) as an acetate salt or in ethanol to give the free base, 7a.

The most preferred embodiment of the present invention is set forth below in Reaction Scheme II.

REACTION SCHEME II

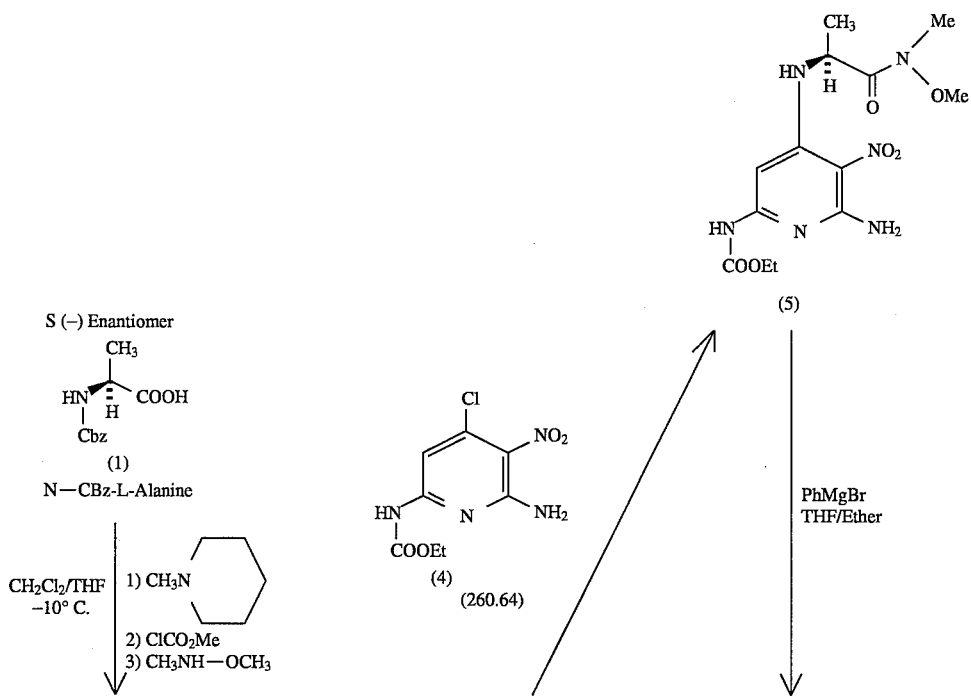

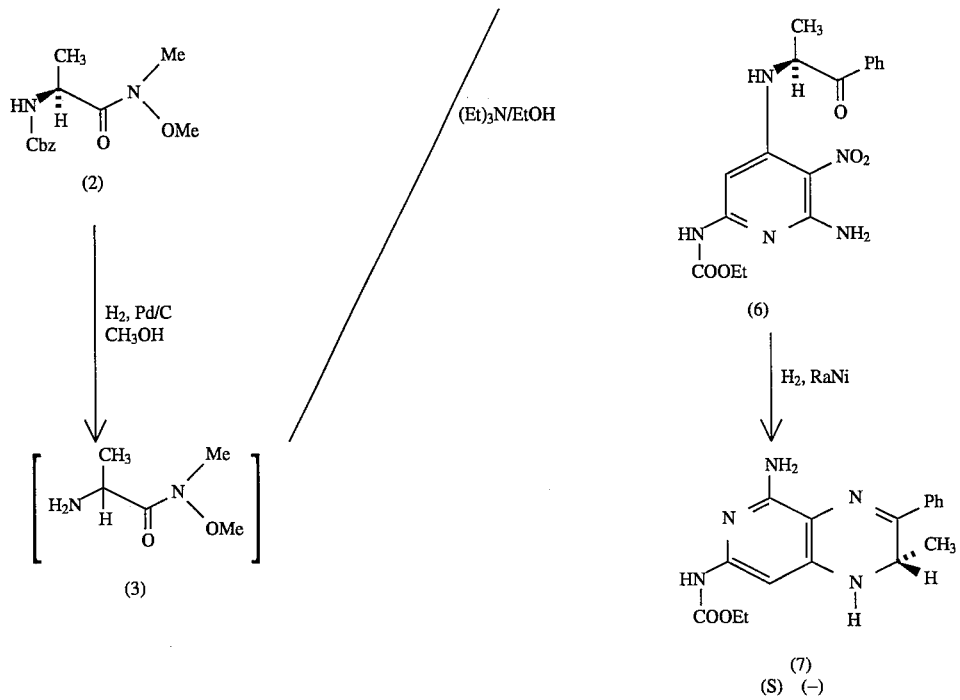

In the above Reaction Scheme II, Cbz is carbobenzyloxy, Ph is phenyl, THF is tetrahydrofuran, and all the reactants have their usual meaning as recognized in the art.

When in the above reaction scheme the R(+) enantiomer of N-carbobenzyloxyalanine is substituted for the S(−) enantiomer, the R(+) product corresponding to (7) is obtained.

The compounds represented by formulas (7a) and (7) are described in U.S. Pat. No. 4,866,059, issued Sep. 12, 1989. The compounds are useful as anticancer agents and can be administered in the manner described in the '059 patent. The portions of U.S. Pat. No. 4,866,059 describing the utility of the compounds and the manner of formulating the compounds and, in particular, from column 1, line 7 to column 2, line 33 and from column 3, line 67 through column 4, line 25 are incorporated herein by reference.

Salts of the compounds of formulas (7a) and (7) can be prepared as generally described in U.S. Pat. No. 4,866,059. A particularly preferred salt is the salt formed with isethionic acid, the detailed description of which is set forth in the specific examples below.

As noted above, the compounds represented by formulas I and II are novel compounds and are key intermediates in the preparation of compounds of formula (7a) and (7). The most preferred compounds of formulas I and II are those wherein each of R and $R_1$ is methyl, i.e., the compounds ethyl (S)-[6-amino-4-[[ 2-(methoxymethylamino)-1-methyl-2-oxoethyl]amino]-5-nitro- 2-pyridinyl]carbamate and ethyl (R)-[6-amino-4-[[ 2-(methoxymethylamino)-1-methyl-2-oxoethyl]amino]-5-nitro- 2-pyridinyl]carbamate.

The following examples further illustrate the invention.

EXAMPLE 1

Preparation of Ethyl (+)-(R)-(5-amino-1,2-dihydro-2-methyl-3-phenylpyrido[3,4-b]pyrazin-7-yl) Carbamate Isethionate Step 1—Preparation of Phenylmethyl (R)-[2-methoxymethylamino)- 1-methyl-2-oxoethyl]carbamate A stirred suspension of N,O-dimethylhydroxylamine hydrochloride (102.4 g, 1.05M) in dichloromethane (600 mL) was cooled to −10° C., under $N_2$, and N-methylpiperidine (109.1 g, 1.10M) was added which produced a clear solution. In a separate flask, N-[(phenylmethoxy) carbonyl] -D-alanine (223.2 g, 1M), was dissolved in THF (600 mL). To the clear solution, under a blanket of $N_2$, were added dichloromethane (2 L), and N-methylpiperidine (109.1 g, 1.1M). The solution was cooled to 0° C., vigorously stirred, and methyl chloroformate (99.2 g, 81.1 mL, 1.05M) was added all at once. The mixture was stirred for 10 minutes at 0° C. to −10° C., and the cold N,O-dimethylhydroxylamine solution prepared earlier was transferred to this mixture via a cannula. The mixture was stirred for 1 hour at 0° C. and further for 12 hours without external cooling. The mixture was cooled back to 0° C., and extracted with cold HCl (0.5N, 1 L), saturated $NaHCO_3$ solution (2×1 L), saturated NaCl solution (1 L), and dried ($MgSO_4$). The solution was evaporated to a white solid under high vacuum (0.2 mm) to give 228.3 g (86%) of the above-titled compound, mp 82° C. to 84° C.; IR (KBr): 3288, 1720, 1656, 1616, 1540 $cm^{-1}$.
$^1$H-NMR ($d_6$-DMSO): 7.60 (d, 1H, J=7.6 Hz); 7.36–7.30 (m, 5H); 5.01 (s, 2H); 4.51–4.42 (m, 1H); 3.73 (s, 3H); 3.10 (s, 3H); 1.17 (d, 3H, J=7.1 Hz).

MS (FAB): M+1=267, 223, 206, 178, 159, 139,119, 91.

Elemental analysis: Calcd for $C_{13}H_{18}N_2O_4$: C, 58.64; H, 6.76; N, 10.51. Found: C, 58.70; H, 6.99; N, 10.35.

Step 2—Preparation of (R) 2-Amino-N-methoxy-N-methyl Propanamide

A solution of the compound from Step 1 (120 g, 0.45M) in absolute EtOH (1.2 L) was hydrogenated at 50 psi over 20% Pd/C (5 g). The catalyst was removed, and the solution evaporated to give 102 g (100%) of a colorless viscous oil. This was kept under high vacuum and used without further purification.

Step 3 —Preparation of Ethyl (R)-[6-amino-4-[[2-(methoxymethylamino)- 1-methyl-2-oxoethyl]amino]-5-nitro-2-pyridinyl]carbamate To a stirred solution of the compound from Step 2 (102 g, 0.45M) in absolute ethanol (1.8 L), were added triethylamine (60.6 g, 83.2 mL, 0.6M), and ethyl 2-amino-3-nitro-4-chloropyridine-6-carbamate (126 g, 0.48M). The mixture, under $N_2$ was heated at reflux for 24 hours, evaporated to a residue and dissolved in EtOAc (2 L). The EtOAc solution was extracted with $H_2O$ (2 L). The aqueous layer was back extracted with EtOAc (1 L). The combined EtOAc layers were extracted with $H_2O$ (2×500 mL), saturated NaCl (1 L), and dried ($MgSO_4$). The mixture was evaporated to a residue (152 g), which was chromatographed over $SiO_2$ (Pet Ether: EtOAc 70:30 to 50:50) to give 135 g (84%) of the above-titled compound, mp 95° C.–97° C., $[\alpha]_D^{23}$=–71.6° (C=1.139, $CHCl_3$); IR (KBr): 3467, 3344, 1740, 1670, 1653, 1646, 1604 cm$^{-1}$. $^1$H-NMR ($CDCl_3$): 9.56 (d, 1H, J=6.8 Hz); 7.77 (s, 1H); 6.71 (s, 1H); 4.68–4.59 (m, 1H); 4.21 (q, 2H); 3.86 (s, 3H); 3.27 (s, 3H); 1.54 (d, 3H, J=6.7 Hz); 1.29 (t, 3H, J=7.1 Hz).

Mass (CI): M+1=357, 341, 327, 311, 296, 280, 268.

Elemental analysis: Calcd for $C_{13}H_{20}N_6O_6$: C, 43.82; H, 5.66; N, 23.58. Found: C, 43.58; H, 5.76; N, 23.07.

Step 4 —Preparation of Ethyl (R)-[6-amino-4-[(1-methyl-2-oxo-2-phenylethyl)amino]-5-nitro-2-pyridinyl] carbamate A 1.9M solution of PhMgBr in diethyl ether (3 L) was prepared fresh from magnesium turnings (46.2 g, 1.9M), bromobenzene (298.3 g, 200 mL, 1.9M), and $I_2$ (2.14 g). The dark solution was held under $N_2$. In a separate flask, a solution of the compound from Step 3 (130 g, 0.365M), in anhydrous THF (3 L) was stirred and cooled to 0° C. under $N_2$. The freshly prepared solution of PhMgBr was slowly added via a cannula at 0° C. with vigorous stirring. The dark suspension was stirred for 16 hours at rt. The mixture was quenched by pouring it into saturated $NH_4Cl$ solution (2 L), and the organic layer was separated. The aqueous layer was extracted with EtOAc (2 L). The combined EtOAc layers were washed with $H_2O$ (4×1 L), saturated NaCl solution (1 L), and dried ($MgSO_4$). After evaporation of the solvent, the residue (180 g) was chromatographed over $SiO_2$ (Pet Ether: EtOAc, 7:3 to 1:1) to give 62.5 g (46%) of the above-titled compound, mp 95° C.–97° C., softens at 90° C. HPLC: 89% $[\alpha]_D^{23}$=–32° (1.01% in $CHCl_3$); IR (KBr): 3477, 3344, 1740, 1717, 1695, 1690, 1685, 1599, 1576, 1563, 1559, 1418, 1300, 1278, 1255, 1211, 1096, 972, 702 cm$^{-1}$.

$^1$H-NMR($CDCl_3$): δ 10.04 (d, 1H, J=6.1 Hz); 8.04 (d, 2H, J=7.2 Hz); 7.68–7.51 (m, 3H); 6.86 (S, 1H); 5.31–5.19 (m, 1H); 4.23 (q, 2H); 1.61 (d, 3H, J=7 Hz); 1.32 (d, 3H, J=7.1 Hz).

MS (CI) M+1=374, 358, 326, 324, 310, 278, 268.

Step 5 —Preparation of Ethyl (+)-(R)-(5-amino-1,2-dihydro- 2-methyl-3-phenylpyrido[3,4-b]pyrazin-7-yl)carbamate Isethionate A solution of (6a) (52 g, 0.139M) in absolute EtOH (1 L) was hydrogenated (50 psi) over RaNi (10 g) for 36 hours. The catalyst was removed, and the solvent evaporated to give a brown foam (48.9 g). This was chromatographed over $SiO_2$ (Pet Ether: EtOAc 1:1) to give 25.7 g (56%) of ethyl (+)-(R)-(5-amino- 1,2-dihydro-2-methyl-3-phenylpyrido[3,4-b]pyrazin-7-yl)carbamate as a yellow solid, mp 148° C.–151° C. (soft at 120° C.) HPLC: 92%, $[\alpha]_D^{23}$=+547° (C=1.154% $CHCl_3$); IR (KBr): 3392, 2976, 1733, 1728, 1719, 1702, 1611, 1579 cm$^{-1}$. $^1$H-NMR ($CDCl_3$): δ 8.21 (bm, 1H); 7.94–7.9 (m, 2H); 7.46–7.40 (m, 3H); 6.72 (s, 1H); 5.24 (bs, 2H); 4.82–4.79 (m, 1H); 4.53 (bs, 1H); 4.22 (q, 2H); 1.33–1.25 (m, 6H).

Mass (CI): M+1=326, 325, 310, 280, 264, 251, 238.

Elemental analysis: Calcd for $C_{17}H_{19}N_5O_2$: C, 62.76; H, 5.89; N, 21.52. Found: C, 63.07; H, 5.95; N, 19.59.

To a solution of the carbamate obtained above (18.95 g, 58.2 mM) in methanol (200 mL), was added a methanolic solution of isethionic acid (0.168N, 329 mL, 55.3 mM) with stirring. After 1 hour, the solvent was evaporated, and the remaining dark foam dissolved in acetonitrile (440 mL) under argon, and with slight warming. The solution was filtered and allowed to stand at rt to give fine yellow-brown crystals, 15.7 g (56%), HPLC: 96%. Further purification was achieved by redissolving 13.5 g (29.9 mM) of 7a isethionate salt in acetonitrile (700 mL) at reflux in the presence of ascorbic acid (0.7 g). The solution was filtered hot and cooled slowly to give 9.7 g of fine yellow-brown crystalline product, mp 164° C.–167° C. HPLC 98.5%, Chiral HPLC: 100%, $[\alpha]_D^{23}$=+394° (C=0.972, MeOH); IR (KBr): 3434, 3420, 3295, 3285, 3273, 3192, 3186, 3173, 3162, 3158, 3148, 2980, 1727, 1662, 1635, 1607, 1591, 1572, 1533, 1467, 1448, 1250, 1222, 1215, 1182, 1148, 1124, 1068, 1035, 696 cm$^{-1}$. $^1$H-NMR ($d_6$-DMSO): δ 11.62 (bs, 1H); 11.05 (bs, 1H); 8.49 (bs, 1H); 8.16–8.14 (m, 2H); 7.71 (bs, 2H); 7.49–7.47 (m, 3H); 5.92 (s, 1H); 5.15–5.08 (m, 1H); 4.24 (q, 2H, J=7 Hz); 3.63 (t, 2H, J=6.7 Hz); 2.62 (t, 2H, J=6.7 Hz); 1.29 (t, 3H, J=7.1 Hz); 1.15 (d, 3H, 6.5 Hz).

MS (FAB). M$^+$+1=325 (451–127=M$^+$—  310, 277, 264, 251, 238, 223, 202, 194, 167, 155, 133, 104, 91, 84, 77, 66, 65, 51, 45.

Elemental analysis: Calcd for $C_{17}H_{19}N_5O_2 \cdot C_2H_6SO_4$: C, 50.54; H, 5.58; N. 15.51, and S, 7.10. Found: C, 50.52; H, 5.46; N, 15.58; S, 6.97.

EXAMPLE 2

Preparation of Ethyl (–)-(S)-(5-amino-1,2-dihydro-2-methyl-3-phenylpyrido[3,4-b]pyrazin-7-yl)carbamate Isethionate Step 1—Preparation of Phenylmethyl (S)-[2-(methoxymethylamino)- 1-methyl-2-oxoethyl]carbamate A stirred suspension of N,O-dimethylhydroxylamine hydrochloride (10.73 g, 110 mM) in dichloromethane (100 mL) was cooled to 0° C. under $N_2$, and N-methylpiperidine (12 g, 14.7 mL, 121 mM) was added which produced a clear solution. In a separate flask, N-[(phenylmethoxy)carbonyl] -L-alanine (24.5 g, 110 mM) was dissolved in THF (100 mL). To the clear solution, under a blanket of $N_2$, were added dichloromethane (200 mL), and N-methylpiperidine (12 g, 14.7 mL, 121 mM). The solution was cooled to –10° C. to –15° C., vigorously stirred, and methyl chloroformate (10.4 g, 8.5 mL, 110 mM) was added all at once. The mixture was stirred for 10 minutes at –10° C. to –15° C., and the N,O-dimethylhydroxylamine solution at 0° C. prepared earlier was transferred to this mixture via a cannula. The mixture was stirred for 1 hour at 0° C. and further for 16 hours without cooling. The reaction mixture was diluted with dichloromethane (200 mL), cooled at 0° C., and extracted with HCl (0.1N, 2×200 mL), saturated $NaHCO_3$ solution (2×100 mL), saturated NaCl solution (200 mL), and dried (MgSO$_4$). The solution was evaporated to a solid under high vacuum (0.02 mm) to give 26.4 g (90%) of the title compound as a white solid, mp 86° C.–88° C.; $[\alpha]_D^{23}=-1.3°$ (C=1.038% in CHCl$_3$); IR (KBr): 3284, 1723, 1719, 1662, 1655 cm$^{-1}$.

$^1$H-NMR (CDCl$_3$): δ 7.35 (s, 5H); 5.55 (d, 1H, J=8 Hz); 5.13 (d, 1H, J=12.2 Hz); 5.06 (d, 1H, J=12.8 Hz); 4.79–4.56 (m, 1H); 3.77 (s, 3H); 3.21 (s, 3H); 1.34 (d, 3H, J=6.7 Hz).

MS (EI) M+1: 267, 223, 207, 206, 178, 151, 134, 107, 92, 91.

Elemental analysis: Calcd for C$_{13}$H$_{18}$N$_2$O$_4$: C, 58.64; H, 6.81; N, 10.52. Found: C, 58.58; H, 6.83; N, 10.42.

Step 2—Preparation of (S)-2-Amino-N-methoxy-N-methyl Propanamide

A solution of the compound from Step 1 (5.4 g, 20.3 mM) in CH$_3$OH (75 mL) was hydrogenated at 50 psi over 20% Pd/C (0.5 g) for 1.5 hours. The catalyst was removed and the solution evaporated to give 4.6 g (100%) of a colorless viscous oil. This was kept under high vacuum and used without further purification.

Step 3—Preparation of Ethyl (S)-[6-amino-4-[[ 2-(methoxymethylamino)-1-methyl-2-oxoethyl]amino]-5-nitro-2-pyridinyl]carbamate To a stirred solution of the compound from Step 2 (4.6 g, 20 mM) in absolute ethanol (100 mL) were added triethylamine (2.5 g, 3.45 mL, 25 mM), and ethyl 2-amino-3-nitro-4-chloropyridine-6-carbamate (5.5 g, 21 mM). The mixture, under N$_2$, was heated at reflux for 19 hours, evaporated to a residue, and dissolved in EtOAc (100 mL). The EtOAc solution was washed with H$_2$O (2×50 mL), and dried (MgSO$_4$). The mixture was evaporated to a residue (8.5 g), which was chromatographed over SiO$_2$ (Pet Ether: EtOAc 3:2 to 2:3) to give 6 g (70%) of the title compound, mp 85° C.–92° C.; $[\alpha]_D^{23}=+69.3°$ (C 1.1% in CHCl$_3$); IR (KBr): 3333, 1741, 1669, 1597, 1591 cm$^{-1}$. $^1$H-NMR (CDCl$_3$): δ 9.58 (d, 1H, J=5.9 Hz); 7.65 (bs, 1H); 6.71 (s, 1H); 4.68–4.56 (m, 1H); 4.22 (q, 2H); 3.86 (s, 3H); 3.27 (s, 3H); 1.54 (d, 3H, J=6.7 Hz); 1.30 (t, 3H, J=7.3 Hz).

MS (CI), M+1: 357, 356, 341, 323, 311, 280, 269, 268, 252, 223, 222.

Elemental analysis: Calcd for C$_{13}$H$_{20}$N$_6$O$_6$: C, 43.82; H, 5.66; N, 23.58. Found: C, 43.62; H, 5.49; N, 23.02.

Step 4—Preparation of Ethyl (S)-[6-amino-4-[(1-methyl-2-oxo-2-phenylethyl)amino]-5-nitro-2-pyridinyl]carbamate A 0.74M solution of phenyl magnesium bromide in ether was freshly prepared from magnesium turnings (26.7 g, 1.1M), bromobenzene (157 g, 105.3 mL, 1M) in diethyl ether (1 L). The mixture was filtered under N$_2$ to remove unreacted magnesium. An aliquot of the solution was titrated against sec-butanol using phenanthroline as an indicator to determine molarity (0.74M), (J Organometallic Chem, 1967;9:165). In a separate flask, a solution of the compound from Step 3 (3.8 g, 10.7 mM) in anhydrous THF (200 mL) was stirred under N$_2$ at rt. The solution of PhMgBr (0.74M) was added in six portions (6×14.3 mL) at 15-minute intervals with vigorous stirring. The dark suspension was stirred 14 hours at rt. The mixture was poured into saturated NH$_4$Cl solution (250 mL) and the organic layer was separated. The aqueous layer was extracted with EtOAc (2×200 mL). The combined organic layers were washed with H$_2$O (2×200 mL), saturated NaCl (100 mL), and dried (MgSO$_4$). After evaporation of solvent, the residue (4.54 g) was chromatographed over SiO$_2$ (Pet Ether: EtOAc 1:1) to give 1.94 g (49%) of the compound named above, mp 102° C.–106° C.; $[\alpha]_D^{23}=+35°$ (1.025% in CHCl$_3$); IR (KBr): 3421, 1740, 1736, 1718, 1695, 1685, 1677, 1653, 1599 cm$^{-1}$. $^1$H-NMR (CDCl$_3$): δ 9.94 (s, 1H); 9.78 (d, 1H, J=6.2 Hz); 8.08 (d, 2H, J=7.2 Hz); 7.76–7.59 (m, 3H); 6.76 (s, 1H); 5.48–5.43 (m, 1H); 4.12 (q, 2H); 1.47 (d, 3H, J=6.8 Hz); 1.22 (t, 3H, J=7.2 Hz).

Mass (FAB): M+1=374.1, 358, 329, 302, 268, 252, 223.

Elemental analysis: Calcd for C$_{17}$H$_{19}$N$_5$O$_5$: C, 54.64; H, 5.09; N, 8.75. Found: C, 54.78; H, 5.11; N, 18.71.

Step 5—Preparation of Ethyl (−)-(S)-(5-amino-1,2-dihydro-2-methyl-3-phenyl-pyrido[3,4-b]pyrazin-7-yl)carbamate Isethionate A solution of the compound from Step 4 (1.67 g, 4.5 mM) in absolute EtOH (100 mL) was hydrogenated (50 psi) over RaNi (0.5 g) for 1.5 hours. The catalyst was removed, and the solvent evaporated to give ethyl (−)-(S)-(5-amino-1,2-dihydro-2-methyl-3-phenylpyrido [3,4-b]pyrazin-7-yl) carbamate as a yellow foam, 1.36 g (93%), HPLC 94%, Chiral HPLC 95.6%, and 3.8% of the R-enantiomer. IR (KBr): 3407, 3397, 3391, 3374, 2975, 1733, 1724, 1719, 1701, 1611, 1578, 1558, 1539, 1533, 1497, 1446, 1410, 1220 cm$^{-1}$. $^1$H-NMR (CDCl$_3$): δ 8.05 (bs, 1H); 7.94–7.91 (m, 2H); 7.46–7.41 (m, 3H); 6.72 (s, 1H); 5.19 (bs, 2H); 4.85–4.77 (m, 1H); 4.50 (s, 1H); 4.22 (q, 2H) A 2.57 (bs, 1H); 1.33–1.25 (m, 6H).

Mass (CI): M+1=326.

To a solution of the free base (0.47 g, 1.4 mM) obtained above, in methanol (20 mL), under argon, was added a methanolic solution of isethionic acid (0.153N, 9.0 mL, 1.37 mM). A clear solution was obtained which was filtered. The solvent was evaporated, and the remaining foam was dissolved in acetonitrile (25 mL) at reflux. The solution was filtered hot and cooled slowly to give fine yellow-brown crystals, which after drying weighed 0.46 g (74%), HPLC: 97%, Chiral HPLC 97.2%, mp 164° C.–166° C.; $[\alpha]_D^{23}=-394°$ (0.886% in CH$_3$OH) The product may be further purified by chromatography of the free base over SiO$_2$ (hexane:EtOAc 6:4) to 99.5% chemical purity and reformation of the isethionate salt as described above. IR (KBr): 3444, 3435, 3429, 3422, 3306, 3295, 3284, 3270, 3263, 3256, 3243, 3227, 3199, 3187, 3164, 3149, 1727, 1658, 1635, 1607, 1591, 1534, 1448, 1251, 1218, 1212, 1182, 1149, 1123, 1068, 1035, 696 cm$^{-1}$. $^1$H-NMR (DMSO): δ 11.60 (bs, 1H); 11.00 (s, 1H); 8.51 (d, 1H, J=2 Hz); 8.17–8.14 (m, 2H); 7.72 (bs, 2H); 7.49–7.47 (m, 3H); 5.97 (s, 1H); 5.14–5.10 (m, 1H); 4.24 (q, 2H); 4.14 (bs, 1H); 2.67 (t, 2H, J=6.8 Hz); 2.68 (t, 2H, J=6.8 Hz); 1.29 (t, 3H, J=7.1 Hz); 1.20 (d, 3H, J=6.5 Hz).

MS (FAB): M+1=325 (451–127), 310, 296, 279, 278, 264, 252, 238, 221, 210, 194, 167.

Elemental analysis: Calcd for C$_{17}$H$_{19}$N$_5$O$_2$.C$_2$H$_6$O$_4$S: C, 50.54, H, 5.58; N, 15.51; S, 7.10. Found: C, 50.71; H, 5.67; N, 15.50; S, 6.84.

We claim:

1. A compound of the formula

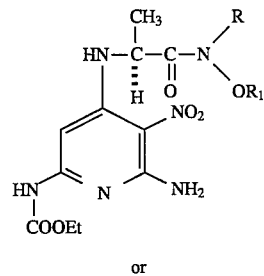

or

-continued
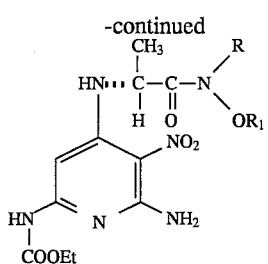
II
wherein each of R and R₁ is a lower alkyl group having from 1 to 4 carbon atoms.
2. A compound of claim 1 which is ethyl (S)-[6-amino-4-[[2-(methoxymethylamino)-1-methyl- 2-oxoethyl]amino]-5-nitro-2-pyridyl]carbamate or ethyl (R)-[6-amino-4-[[2-(methoxymethylamino)-1-methyl- 2-oxoethyl]amino]-5-nitro-2-pyridinyl]carbamate.
* * * * *